United States Patent [19]

Goel et al.

[11] 4,126,637

[45] Nov. 21, 1978

[54] PROCESS FOR THE PRODUCTION OF 2,2-DIMETHYL-5-(2,5-XYLYLOXY)VALERIC ACID

[75] Inventors: Om P. Goel, Canton; William M. Pearlman, Ann Arbor, both of Mich.

[73] Assignee: Warner-Lambert Company, Morris Plains, N.J.

[21] Appl. No.: 807,468

[22] Filed: Jun. 17, 1977

[51] Int. Cl.$^2$ ............................................. C07C 65/02
[52] U.S. Cl. .................................................. 562/421
[58] Field of Search ............ 260/520 C, 521 R, 523 A

[56] References Cited

U.S. PATENT DOCUMENTS

| | | | |
|---|---|---|---|
| 3,452,081 | 6/1969 | Sprague et al. | 260/521 R |
| 3,674,836 | 4/1972 | Creger | 260/521 R |

*Primary Examiner*—James O. Thomas, Jr.
*Assistant Examiner*—G. T. Breitenstein
*Attorney, Agent, or Firm*—David B. Ehrlinger; Stephen Raines; Frank S. Chow

[57] ABSTRACT

A process is provided for the production of 2,2-dimethyl-5-(2,5-xylyloxy)valeric acid which comprises subjecting 2,2-dimethyl-5-(2,5-xylyloxy)valeraldehyde to oxidation with elemental oxygen in a three-phase reaction mixture comprising a water immiscible organic solvent for said valeraldehyde, an aqueous alkaline solution, and a noble metal catalyst.

10 Claims, No Drawings

PROCESS FOR THE PRODUCTION OF 2,2-DIMETHYL-5-(2,5-XYLYLOXY)VALERIC ACID

SUMMARY AND DETAILED DESCRIPTION

This invention relates to a process for the production of 2,2-dimethyl-5-(2,5-xylyloxy)valeric acid (a pharmacologic agent which is useful for reducing serum triglyceride levels described in U.S. Pat. No. 3,674,836) from 2,2-dimethyl-5-(2,5-xylyloxy)valeraldehyde. More particularly, the invention relates to such process involving catalytic oxidation in a unique oxidation system.

The oxidation of 2,2-dimethyl-5-(2,5-xylyloxy)-valeraldehyde to 2,2-dimethyl-5-(2,5-xylyloxy)valeric acid presents a difficult problem in that the hindered α-disubstituted aldehyde function must be selectively oxidized without affecting the readily oxidizable aromatic methyl group substituents. Thus, any of the common chemical oxidizing agents such as potassium permanganate, hydrogen peroxide, etc., under a variety of known conditions gives complex mixtures in which the desired product 2,2-dimethyl-5-(2,5-xylyloxy)valeric acid is only one of several products formed, from which complex mixtures the desired product cannot be easily isolated.

According to the present invention, there is provided a workable process for the production of 2,2-dimethyl-5-(2,5-xylyloxy)valeric acid which comprises subjecting 2,2-dimethyl-5-(2,5-xylyloxy)valeraldehyde to oxidation with elemental oxygen in a three-phase reaction mixture comprising a water-immiscible organic solvent for said valeraldehyde, an aqueous alkaline solution, and a noble metal catalyst. In a preferred procedure, the product is isolated by acidification of the aqueous phase by which means the product separates cleanly and easily as a solid phase. Advantageously, the oxidation process is rapid and complete; there is no unoxidized aldehyde remaining. The presence of aqueous alkaline solution not only helps to protect the product from further oxidation by removing it from further oxidation from the organic phase but during work up in production equipment provides for safety of operation. The yield of desired product typically is in the range of about 70 to 75%. The oxidizing agent may be pure oxygen gas or air or similar oxygen-containing gaseous mixtures, the same being sometimes referred to hereinafter as elemental oxygen. Oxygen gas alone is preferred as it affords better yields. The reaction is carried out under moderate pressure, that is at pressures from about 10-50 pounds per square inch and preferably about 25 pounds per square inch. A mere bubbling of oxygen into the reactive mixture, even for prolonged periods of time, typically is not productive. As indicated, a noble metal catalyst is used for the reaction. Any noble metal catalyst such as 5-10% platinum on carbon or 5-20% palladium on carbon or 5-10% gold on carbon or any mixture of these may be used for this purpose. A finely divided precipitate of gold on carbon is preferred as catalyst. The catalyst is freshly made and is made by known techniques. Gold as catalyst provides a more moderate rate of oxidation than platinum or palladium. Thus, reaction completion times are about 10 minutes using gold on carbon and 1-2 minutes using either platinum on carbon or palladium on carbon. In the typical run performed under oxygen pressure of 25 pounds per square inch in a mechanical shaker, there is an induction period following which there is a rapid rise in temperature and drop in pressure. The reaction is normally carried out at ambient temperature, that is at 20°-25° C. No heating is necessary. The reaction can be moderated by cooling of the reaction mixture during the period of rapid uptake of oxygen. Any of various water-immiscible organic solvents can be used for the reaction such as n-hexane, n-heptane, n-octane, ethyl acetate, chloroform, dichloromethane and mixtures of these solvents. A preferred solvent is n-heptane.

The aqueous alkaline solution employed in the reaction, preferably an alkali metal (especially potassium or sodium) salt solution, is such that during the reaction it serves to convert the 2,2-dimethyl-5-(2,5-xylyloxy)valeric acid to its salt form in the aqueous phase.

The invention is illustrated by the following examples.

EXAMPLE 1

A solution of 23.4 g. (0.1 mole) of 2,2-dimethyl-5-(2,5-xylyloxy)valeraldehyde in 100 ml. of n-heptane and a solution of 14 g. of potassium carbonate in 300 ml. of water was introduced into a stainless steel pressure flask. A 3 g. quantity of freshly prepared 5% Au/C catalyst was added. The reaction flask was fitted on to a mechanical shaker and pressurized with 26.4 psi of oxygen at a temperature of 22° C. After an induction period (about 65 minutes), there was a rapid uptake of oxygen over 10 minutes as the temperature rose to 36.5° C. The pressure stabilized at 22 psi, a drop of 4.4 psi, equivalent to the uptake of 0.055 mole of oxygen. The reaction mixture was removed, catalyst filtered, and the lower aqueous phase removed. The organic layer was extracted with 10% aqueous alkali and the extract combined with the original aqueous phase. Acidification of the aqueous phase with conc. HCl precipitated an oil which readily crystallized. The crystalline product, 2,2-dimethyl-5-(2,5-xylyloxy)valeric acid, was filtered, washed, dried and purified by recrystallization from methanol-water mixture; m.p. 58°-59° C.; yield: 17.5 g.

EXAMPLE 2

The procedure of the above example was followed except that the 5% Au/C was replaced with a coprecipitated mixture of 0.75 g., 20% Pd/C and 0.25 g. of 10% Au/C. After an induction period there was a rapid rise in temperature (27° C. to 46° C.) and a drop in pressure. The oxidation was complete in less than 1 minute. The yield of 2,2-dimethyl-5-(2,5-xylyloxy)valeric acid was 18.6 g.

EXAMPLE 3

The procedure of Example 1 was followed except that the catalyst was replaced with 1 g. of freshly prepared 10% Pt/C. The yield of 2,2-dimethyl-5-(2,5-xylyloxy)valeric acid was 17.2 g.

EXAMPLE 4

The procedure of Example 1 was followed except that the catalyst was replaced with 1 g. of freshly prepared 20% Pd/C. After an induction period, the oxidation was complete in less than 1 minute with temperature rise of 25° to 36° C. The yield of 2,2-dimethyl-5-(2,5-xylyloxy)valeric acid was 17 g.

We claim:

1. Process for the production of 2,2-dimethyl-5-(2,5-xylyloxy)valeric acid which comprises subjecting 2,2-dimethyl-5-(2,5-xylyloxy)valeraldehyde to oxidation with elemental oxygen at pressures from about 10-50 pounds per square inch in a three-phase reaction mixture comprising a water immiscible organic solvent for said valeraldehyde, an aqueous alkaline solution, and at least a catalytic amount of at least one noble metal catalyst selected from the group consisting of gold, platinum and palladium.

2. Process according to claim 1 in which the aqueous phase is acidified and 2,2-dimethyl-5-(2,5-xylyloxy)valeric acid is recovered therefrom.

3. Process according to claim 1 in which the aqueous phase is acidified and 2,2-dimethyl-5-(2,5-xylyloxy)valeric acid is recovered therefrom as a solid phase.

4. Process according to claim 1 in which the elemental oxygen is in the form of pure oxygen gas.

5. Process according to claim 1 in which the reaction is carried out at a pressure of about 25 pounds per square inch.

6. Process according to claim 1 in which the noble metal catalyst comprises gold on carbon.

7. Process according to claim 1 in which the noble metal catalyst comprises platinum on carbon.

8. Process according to claim 1 in which the noble metal catalyst comprises palladium on carbon.

9. Process according to claim 1 in which the solvent is n-heptane.

10. Process according to claim 1 in which the aqueous alkaline solution is an aqueous alkali metal salt solution.

* * * * *